United States Patent [19]
Lang et al.

[11] Patent Number: 4,822,375
[45] Date of Patent: Apr. 18, 1989

[54] DYEING COMPOSITIONS FOR KERATINOUS FIBRES BASED ON INDOLE DERIVATIVES, AND NEW COMPOUNDS

[75] Inventors: Gérard Lang, Saint-Gratien; Hervé Richard; Madeleine Leduc, both of Paris; Alex Junino, Livry-Gargan, all of France

[73] Assignee: L'Oreal, Paris, France

[21] Appl. No.: 21,932

[22] Filed: Mar. 5, 1987

[30] Foreign Application Priority Data

Mar. 6, 1986 [LU] Luxembourg .......................... 86346

[51] Int. Cl.$^4$ .................... A61K 7/13; C07D 209/30; C07F 9/12
[52] U.S. Cl. .......................................... 8/423; 8/408; 8/409; 8/429; 548/414; 548/430; 548/469; 548/492; 548/493
[58] Field of Search .................. 8/408, 423, 429, 409; 548/469, 492, 493, 414, 430

[56] References Cited

U.S. PATENT DOCUMENTS

| | | | |
|---|---|---|---|
| 3,194,734 | 7/1965 | Seemuller et al. | 8/423 |
| 3,976,639 | 8/1976 | Batcho et al. | 260/240 R |
| 4,013,404 | 3/1977 | Parent et al. | 8/423 |
| 4,127,501 | 11/1978 | Wang et al. | 252/403 |
| 4,208,183 | 6/1980 | Grollier et al. | 8/409 |

FOREIGN PATENT DOCUMENTS

2536993 6/1984 France .

OTHER PUBLICATIONS

Chemical Abstracts, vol. 75, 1971, p. 209, 118189v, Merchant et al.
Journal of Chromatography, vol. 222, 1981, pp. 329-336, Pavel et al.
J. Org. Chem., vol. 48, 1983, pp. 3347-3349, Sinhababu et al.
J. Med. Chem., vol. 25, 1982, pp. 263-271, Borchardt et al.

*Primary Examiner*—Paul Lieberman
*Assistant Examiner*—Linda Skaling
*Attorney, Agent, or Firm*—Cushman, Darby & Cushman

[57] ABSTRACT

Dyeing compositions for keratinous fibres based on indole derivatives, and new compounds.

Dyeing composition for keratinous fibres, and especially human hair, characterized in that it contains, in a cosmetically acceptable medium suitable for dyeing these fibres, at least one dye corresponding to the formula:

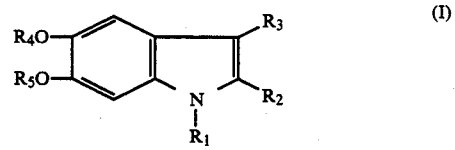

in which $R_1$ denotes a hydrogen atom or a lower alkyl group or a group —$SiR_9R_{10}R_{11}$;
$R_2$ and $R_3$, which may be identical or different, denote a hydrogen atom, a lower alkyl group, a carboxyl group, a lower alkoxycarbonyl group or a group -COOSiR$_9$- R$_{10}$R$_{11}$; and R$_5$, which may be identical or different, denote at least one linear or branched $C_1$-$C_{20}$ alkyl group, a formyl group, a linear or branched $C_2$-$C_{20}$ acyl group, a linear or branched $C_3$-$C_{20}$ alkenoyl group, a group —$SiR_9R_{10}R_{11}$, a group —$P(O)(OR_6)_2$ or a group $R_6OSO_2$—, the other group $R_4$ or $R_5$ being able to be a hydrogen atom, $R_4$ and $R_5$ are not simultaneously acetyl, or alternatively $R_4$ and $R_5$, together with the oxygen atoms to which they are attached, form a ring optionally containing a carbonyl group, a thiocarbonyl group, a group >P-(O)OR$_6$ or >CR$_7$R$_8$;
$R_6$ denoting a hydrogen atom or a lower alkyl group, $R_7$ denoting a hydrogen atom or a lower alkyl group, and $R_8$ denotes a lower alkoxy group or a mono- or dialkylamino group, $R_9$, $R_{10}$ and $R_{11}$, which may be identical or different, denoting linear or branched lower alkyl groups, and the cosmetically acceptable salts of alkali metals, alkaline earth metal metals, ammonia or amines.

25 Claims, No Drawings

DYEING COMPOSITIONS FOR KERATINOUS FIBRES BASED ON INDOLE DERIVATIVES, AND NEW COMPOUNDS

The present invention relates to new dyeing compositions intended for the dyeing of keratinous fibres, and especially human hair, based on indole derivatives, and to the new compounds used in these compositions.

Dyes of the indole family, and especially 5,6-dihydroxyindole, are well known and have already been used in hair dyeing. The use of this type of compound forms the subject of French Pat. Nos. 1,264,707, 1,133,594 and 1,166,172 of the Applicant, and also of French patent application No. 2,536,993.

The Applicant has discovered that a special class of indoles possessed advantageous dyeing properties for keratinous fibres, and especially human hair, these compounds possessing, moreover, the advantage of being stable in the dyeing media generally used for the application of dyes based on 5,6-dihydroxyindoles. In contrast to 5,6-dihydroxyindole, which leads to tints which are black or more or less grey, the special class of indoles according to the invention enables lighter and more natural shades to be obtained which are light-fast and weather-resistant.

The subject of the invention is hence new dyeing compositions for keratinous fibres and especially for human hair, based on certain indole derivatives.

Another subject of the invention consists of the new compounds derived from indole which can be used in these compositions.

The subject of the invention is finally a dyeing process employing these compounds and the compositions containing them.

Other subjects of the invention will emerge on reading the description and the examples which follow.

The compositions according to the invention are essentially characterized in that they contain, in a cosmetic medium suitable for dyeing keratinous fibres, and especially human hair, at least one dye corresponding to the formula:

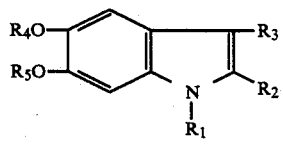

in which $R_1$ denotes a hydrogen atom or a lower alkyl group or a group $-SiR_9R_{10}R_{11}$;

$R_2$ and $R_3$, which may be identical or different, denote a hydrogen atom or alternatively a lower alkyl group, a carboxyl group, a lower alkoxycarbonyl group or a group $-COOSiR_9R_{10}R_{11}$;

$R_4$ and $R_5$, which may be identical or different, denote at least one linear or branched $C_1-C_{20}$ alkyl group, a formyl group, a linear or branched $C_2-C_{20}$ acyl group, a linear or branched $C_3-C_{20}$ alkenoyl group, a group $-SiR_9R_{10}R_{11}$, a group $-P(O)(OR_6)_2$ or a group $-R_6OSO_2-$, the other substituent $R_4$ being able to denote a hydrogen atom, $R_4$ and $R_5$ are not simultaneously an acetyl group, or alternatively $R_4$ and $R_5$, together with the oxygen atoms to which they are attached, form a ring optionally containing a carbonyl group, a thiocarbonyl group, a group $>P(O)OR_6$ or a group $>CR_7R_8$;

$R_6$ denoting a hydrogen atom or a lower alkyl group, $R_7$ denoting a hydrogen atom or a lower alkyl group, $R_8$ denoting a lower alkoxy group or a mono- or dialkylamino group, and $R_9$, $R_{10}$ and $R_{11}$, which may be identical or different, denoting linear or branched lower alkyl groups, and the corresponding salts of alkali metals, alkaline earth, ammonia and amines.

In the groups defined above, a lower alkyl or lower alkoxy group preferably denotes a group having 1 to 6 carbon atoms.

Among the compounds of formula (I), there may be mentioned the following compounds which appear in Table 1.

TABLE I

| No. | Name of compound | Melting point and boiling point (b.p.) °C. |
|---|---|---|
| 1 | 6-Hydroxy-5-methoxyindole | 111° |
| 2 | 5-Hydroxy-6-methoxyindole | 116° |
| 3 | 6-Acetoxy-5-methoxyindole | 140° |
| 4 | (5 or 6)-Acetoxy-(6 or 5)-hydroxyindole | 184° |
| 5 | 5,6-Carbonyldioxyindole | 180° |
| 6 | (5 or 6)-Formyloxy-(6 or 5)-hydroxyindole | 161° |
| 7 | (5 or 6)-Acetoxy-(6 or 5)-formyloxyindole | — |
| 8 | 6-Formyloxy-5-methoxyindole | 118° |
| 9 | 5-Butoxy-6-hydroxyindole | 91° |
| 10 | 6-Butoxy-5-hydroxyindole | 105° |
| 11 | (5 or 6)-Hydroxy-(6 or 5)-trimethylsilyloxyindole | 97° |
| 12 | 5,6-Bis(trimethylsilyloxy)indole | 67° *b.p. 151° |
| 13 | 5,6-[(1-Ethoxyethylidene)dioxy]indole | 69° *b.p. 160° |
| 14 | 5,6-Dihydroxyindole cyclic phosphodiester | >260° |
| 15 | 5,6-Thiocarbonyldioxyindole | >260° |
| 16 | 5-Methoxy-6-trimethylsilyloxyindole | 90–91° |
| 17 | 5,6-Bis(trimethylsilyloxy)-2-methylindole | 99° |
| 18 | 5,6-Carbonyldioxy-2-methylindole | 143° |
| 19 | (5 or 6)-Hydroxy-(6 or 5)-myristoyloxyindole | 125–126° |
| 20 | 5,6-Dimyristoyloxyindole | 92° |
| 21 | (5 or 6)-Hydroxy-(6 or 5)-oleoyloxyindole | 94–100° |
| 22 | 5,6-Dioleoyloxyindole | 38–40° |
| 23 | 5,6-Bis(trimethylsilyloxy)-2-carbethoxyindole | 143° |
| 24 | 5,6-Bis(trimethylsilyloxy)-2-(trimethylsilyloxycarbonyl)indole | 173° |
| 25 | 5,6-Bis(trimethylsilyloxy)-3-methyindole | 84° |
| 26 | 6-Hexadecyloxy-5-methoxyindole | 68.5° |
| 27 | 6-Hexadecyloxy-5-hydroxyindole | 80° |
| 28 | 5-Hexadecyloxy-6-hydroxyindole | 79° |
| 29 | 5,6-Dipivaloyloxyindole | 139° |
| 30 | (5 or 6)-Hydroxy-(6 or 5)-pivaloyloxyindole | 130° |
| 31 | 5,6-Dihexanoyloxyindole | 60–63° |
| 32 | (5 or 6)-Hexanolyloxy-(6 or 5)-hydroxyindole | 88° |
| 33 | 5,6-Dibutanoyloxyindole | 74° |
| 34 | (5 or 6)-Butanoyloxy-(6 or 5)-hydroxyindole | 121° |

*at $1.06 \times 10^2$ Pa.

The especially preferred compounds correspond to the formula (I) in which $R_1$ denotes a hydrogen atom, $R_2$ and $R_3$, which may be identical or different, denote a hydrogen atom or a lower alkyl group, $R_4$ or $R_5$ denotes a linear or branched $C_1-C_{20}$ alkyl group, a linear or branched $C_2-C_{20}$ acyl group or a linear or branched $C_3-C_{20}$ alkenoyl group, the other denoting hydrogen, or alternatively $R_4$ and $R_5$ simultaneously denote $SiR_9R_{10}R_{11}$ where $R_9$, $R_{10}$ and $R_{11}$ have the meanings stated above.

The compounds of formula I are preferably present in the composition according to the invention in proportions of between 0.01 and 5% by weight, relative to the total weight of the composition, and preferably between 0.03 and 2.5%.

The compositions which are usable according to the invention are liquid compositions thickened to a greater or lesser extent, creams, gels, oils or powders to be diluted with liquids at the time of use, also known as cataplasms. These compositions can also be present in one or two-compartment outfits or kits containing the different components intended for mixing at the time of use.

When the composition is presented in a single pack, the cosmetic medium is essentially aqueous and has a pH which can vary between 3.5 and 11, and preferably between 5 and 10.5. It is adjusted to the desired value using alkalinizing or acidifying agents which are known per se.

These compositions can contain surfactants, present in proportions of between 0.1 and 55% by weight, and preferably between 1 and 40% by weight, relative to the total weight of the composition.

These aqueous compositions can also contain organic solvents which are acceptable from the cosmetic standpoint, among which there may be mentioned, by way of example, $C_1-C_4$ lower alcohols such as ethanol, isopropanol, and tert-butyl alcohol, ethylene glycol monomethyl, monoethyl or monobutyl ethers, and ethylene glycol monoethyl ether acetate.

These solvents are preferably used in proportions ranging from 1 to 60% by weight, and more especially from 3 to 30% by weight, relative to the total weight of the composition.

These compositions can also contain anionic, nonionic, cationic or amphoteric polymers or mixtures thereof, in proportions from 0.1 to 5% by weight relative to the total weight of the composition.

They can be thickened with agents chosen from sodium alginate, gum arabic, guar or carob gum, biopolymers such as zanthan gum, pectins, cellulose derivatives such as methylcellulose, hydroxymethylcellulose, hydroxypropylcellulose, carboxymethylcellulose and various polymers having thickening functions such as acrylic acid derivatives. It is also possible to use inorganic thickening agents such as bentonite.

These thickening agents are preferably present in proportions of between 0.1 and 5% by weight, and especially between 0.5 and 3% by weight, relative to the total weight of the composition.

These compositions can naturally contain other additives customarily used in compositions for dyeing the hair, such as penetrating agents, swelling agents, seqestering agents, antioxidants, buffers, electrolytes, perfumes, and the like.

An embodiment of the invention can consist in using an anhydrous medium, that is to say a medium not containing more than 1% of water. Such a composition is intended for mixing, in the instant before use, with an aqueous cosmetic medium as defined above.

The anhydrous medium consists, according to this variant of the invention, of an anhydrous solvent chosen from saturated monohydric alcohols such as ethanol, isopropanol or tert-butyl alcohol, ethylene glycol monomethyl, monoethyl or monobutyl ether or ethylene glycol monoethyl ether acetate.

The process for dyeing keratinous fibres, and especially human hair, according to the invention can be carried out in different variants.

According to one variant, an acidic or neutral composition containing at least one of the dyes of formula (I) can initially be applied on the hair and, after 5 to 60 minutes' contact of the first composition with the fibres, the hair is wrung dry and a composition capable of causing the oxidation or the development of the dye is applied. For this purpose, it is possible to use either simply the oxygen in the air or else peroxides such as hydrogen peroxide.

Another embodiment can consist in adding an oxidation catalyst, such as, for example, a cobalt, manganese, copper or aluminium salt, to the solution added in the second stage.

Another variant of the invention comprises the application of compounds of formula (I) in an alkaline medium containing, by way of an alkalinizing agent, for example, ammonia or an amine such as monoethanolamine, triethanolamine, morpholine, diethylamine or hydroxylamine. Using these compositions, it is also possible to carry out so-called "progressive" dyeing, consisting in superposing several applications of the composition until the dyeing obtained possesses a darker shade than the initial shade which can be obtained with the composition.

The formation of the dye on the hair can be accelerated by adding, either on the hair or to the composition immediately before use, a solution of an oxidizing agent or of an oxidation catalyst. The oxidizing agent can consist of hydrogen peroxide or alternatively a persalt such as sodium perborate, sodium percarbonate, ammonia persulphate or sodium bromate.

When an oxidation catalyst is used, various metal salts can be employed, such as manganese, cobalt, iron, copper and silver salts. By way of example, there may be mentioned manganese sulphate, manganese lactate, cobalt chloride, ferric chloride, cupric chloride and ammoniacal silver nitrate.

A third variant of the invention consists in bringing the hair into contact with a metal salt before or after the application of the composition containing the dye of formula (I), the hair being rinsed between the two stages. This dyeing process can be followed by bringing the hair into contact, after rinsing, with a hydrogen peroxide solution to lighten, where appropriate, the tint obtained by means of the dye of formula (I).

The metal salts are of the same type as those mentioned above. Copper, iron, cobalt, manganese and aluminium salts and, generally, any salt which promotes the formation of melanin from the dyes of formula (I) are used more especially.

For carrying out the different processes, it is naturally possible to prepare beforehand multi-compartment outfits also known as hair dyeing kits containing, in a single presentation, a plurality of vessels, one of which contains at least the dye of formula (I) in a cosmetically acceptable medium, another the metal salt and the third, where appropriate, the oxidizing agent, In all these embodiments, the medium containing the dye of formula (I) can have the composition stated above.

Among the compounds which are used according to the invention, for dyeing keratinous fibres and especially human hair, some are new and constitute another subject of the invention. These compounds correspond to the general formula

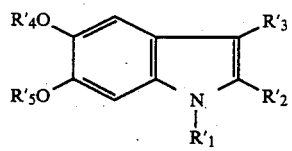

in which $R'_1$ denotes a hydrogen atom or a lower alkyl group; $R'_2$ and $R'_3$, which may be identical or different, denote a hydrogen atom, a lower alkyl group, a carboxyl group, a lower alkoxycarbonyl group or a —COOSi(CH$_3$)$_3$ group; $R'_4$ and $R'_5$, which may be identical or different, can denote a linear or branched $C_9$–$C_{20}$ alkyl group, a linear or branched $C_{10}$–$C_{20}$ acyl group, a linear or branched $C_3$–$C_{20}$ alkenoyl group, a group —P(O)(OR$_6$)$_2$, the other group $R'_4$ or $R'_5$ being able to be a hydrogen atom, a $C_1$–$C_8$ alkyl group, a formyl group, a $C_2$–$C_9$ acyl group or an aralkyl group;

$R'_4$ and/or $R'_5$ being able to denote an —Si(CH$_3$)$_3$ group when $R'_1$ is other than methyl; or alternatively $R'_4$ and $R'_5$ form, with the oxygen atoms to which they are attached, a ring optionally containing a carbonyl group when one of the substituents $R'_1$, $R'_2$ or $R'_3$ is other than hydrogen, a thiocarbonyl group, a group >P(O)OR$_6$ or >CR$_7$R$_8$, R$_6$ denoting a hydrogen atom or a lower alkyl radical, R$_7$ denoting a hydrogen atom or a lower alkyl group and R$_8$ denoting a lower alkoxy group or a mono- or dialkylamino group, and the corresponding salts with alkali metals, alkaline earth metals or amines.

These compounds can be prepared according to processes which are known per se. The 5,6-dihydroxyindole derivatives, substituted or unsubstituted at the 2- and/or 3-positions, can be synthesized from compounds which are already substituted at the 5- and 6-positions, the final stage of formation being a reductive cyclization of a β,2-dinitrostyrene derivative:

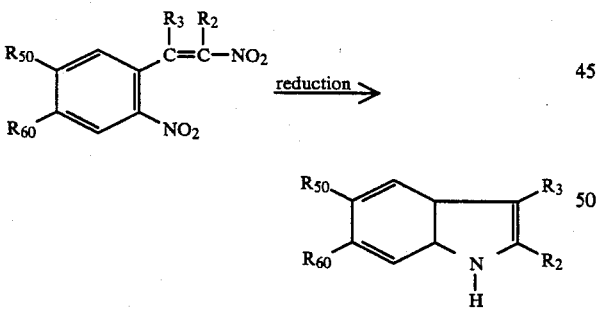

or alternatively the 5,6-dihydroxyindole derivatives substituted at the 1-, 2- and/or 3-positions can be synthesized from 5,6-dihydroxyindoles substituted at the 1-, 2- and/or 3-positions, by methods in which the presence of free bases in the reaction medium is avoided on account of the instability in basic medium of 5,6-dihydroxyindoles substituted at the 1-, 2- and/or 3-positions.

Thus, it is possible to work either by phase transfer, in the case of the etherifications (this being used, in particular, for the compounds 26, 27 and 28), or by transesterification methods in the case of the 5,6-dihydroxyindole esters substituted at the 1-, 2- and/or 3-positions (such as for the compounds 14, 15 and 18 to 22). In these latter cases, the monoacyl and diacyl derivatives are separated by column chromatography.

The examples which follow are intended to illustrate the compounds according to the invention without being limiting in nature.

Table II gives the main characteristics of the absorption spectrum, the numbers referring to those in Table I.

TABLE II

| No. | Solvent | λmax | (εmax) |
|---|---|---|---|
| 1 | Propylene glycol | 300 nm | (5360) |
|   |   | 275 nm | (3780) |
|   |   | 230 nm | (4590) |
| 2 | Propylene glycol | 300 nm | (4020) |
|   |   | 282 nm | (shld.) |
|   |   | 275 nm | (4750) |
|   |   | 230 nm | (6800) |
| 4 | Ethanol | 296 nm | (6500) |
|   |   | 274 nm | (4920) |
| 5 | Ethanol | 294 nm | (8440) |
|   |   | 218 nm | (22200) |
| 8 | Propylene glycol | 296 nm | (5120) |
|   |   | 288 nm | (4800) |
|   |   | 228 nm | (7320) |
| 9 | Ethanol | 302 nm | (3960) |
|   |   | 274 nm | (2950) |
| 10 | Ethanol | 301 nm | (6010) |
|   |   | 274 nm | (3990) |
| 12 | Ethanol | 300 nm | (3800) |
|   |   | 276 nm | (shld. 2950) |
| 13 | Ethanol | 305 nm | (6480) |
|   |   | 274 nm | (3750) |
| 15 | Ethanol | 312 nm | (21400) |
|   |   | 263 nm | (8750) |
| 16 | Ethanol | 298 nm | (6100) |
|   |   | 274 nm | (4400) |
| 17 | Ethanol | 300 nm | (8300) |
|   |   | 275 nm | (5520) |
| 18 | Ethanol | 301 nm | (8170) |
|   |   | 278 nm | (shld. 5370) |
|   |   | 219 nm | (20900) |
| 19 | Ethanol | 296 nm | (6500) |
|   |   | 273 nm | (4860) |
| 20 | Ethanol | 284 nm | (6870) |
|   |   | 220 nm | (29500) |
| 21 | Ethanol | 296 nm | 6730) |
|   |   | 273 nm | (5050) |
| 22 | Ethanol | 284 nm | (7000) |
| 23 | Ethanol | 317 nm | (22000) |
| 26 | Ethanol | 297 nm | (5800) |
|   |   | 273 nm | (3900) |
| 27 | Ethanol | 300 nm | (5990) |
|   |   | 273 nm | (4000) |
| 28 | Ethanol | 300 nm | (6500) |
|   |   | 273 nm | (4170) |
| 29 | Ethanol | 284 nm | (6900) |
| 30 | Ethanol | 295 nm | (6340) |
|   |   | 273 nm | (4700) |
| 31 | Ethanol | 284 nm | (7100) |
| 32 | Ethanol | 295 nm | (6400) |
|   |   | 273 nm | (4910) |
| 33 | Ethanol | 284 nm | (6600) |
| 34 | Ethanol | 295 nm | (6400) |
|   |   | 273 nm | (4380) |

(shld. = shoulder)

PREPARATION EXAMPLES

Example 1

Preparation of the compound No. 5 of Table I
(5,6-Carbonyldioxyindole)

A solution of 7.14 g (0.044 mole) of N,N'-carbonyldiimidazole in 400 ml of hot toluene and 2.01 g (0.0135 mole) of 5,6-dihydroxyindole in 100 ml of isopropyl ether and 50 ml of dry toluene are added simultaneously at 80° C. and under nitrogen to 50 ml of dry toluene (time taken for introduction: 4 hours). The mixture is then kept for 1 hour 30 minutes at 90° C. After cooling, the organic phase is washed twice with water and then dried over sodium sulphate. The filtrate is concentrated in a rotary evaporator. The residue obtained is dissolved in 5 ml of ethanol and reprecipitated in 30 ml of water. 1.96 g (yield: 83%) of a white powder of the derivative 5 is obtained.

Analysis: $C_9H_5NO_3$; Calculated: C 61.72; H 2.88; N 8.00; Found: C 61.38; H 2.89; N 7.89.

Example 2

Preparation of the compound No. 6 of Table I
(5-Farmyloxy-8-hydroxyindole and 6-formyloxy-5-hydroxyindole)

2.39 g (0.0257 mole) of acetic formic anhydride are added dropwise at $-5°$ C. to 1.8 g (0.0122 mole) of 5,6-dihydroxyindole dissolved in 20 ml of dry ether. In the course of 6 hours, the temperature is gradually raised to 20° C. The mixture is left overnight with stirring. A white precipitate is collected which is filtered off and recrystallized in a toluene/acetone (3:2) mixture. The compound 6 is obtained (218 mg; yield: 10%) in the form of a white powder. The compound 6 is a 60:40 mixture of the two formyl derivatives, as shown by the proton NMR spectrum. MS (70 eV) for $C_9H_7NO_3$: 177 ($M^+$, 58.5), 149 (100), 120(17), 103(45) and 65(21).

Example 3

Preparation of the compound No. 7 of Table I
(6-Acetoxy-5-formyloxyindole and 5-acetoxy-6-formyloxyindole)

The above derivative 6 (150 mg; $8.5 \times 10^{-4}$ mole) is stirred for 4 hours with 2.25 ml of acetic anhydride and 0.12 ml of pyridine. After evaporation of the solvents, taking up in dichloromethane, successive washes with 0.1N aqueous HCl and 2% strength aqueous $NaHCO_3$ solutions and water, and drying, the derivative 7 (150 mg; yield: 80%) is obtained which, from the NMR spectrum, is a 60:40 mixture of the two isomers.

Example 4

Preparation of the compound No. 8 of Table I
(6-Formyloxy-5-methoxyindole)

A solution of 12 g (0.0735 mole) of 6-hydroxy-5-methoxyindole and 12.95 g (0.147 mole) of acetic formic anhydride in 100 ml of toluene is brought to reflux for 16 hours under nitrogen. After the mixture is cooled, 30 g of silica 60 are added to the reaction medium, the mixture is filtered and the filtrate concentrated twofold. The white precipitate obtained is filtered off and then recrystallized again in 30 ml of toluene. After being dried under vacuum, 4.2 g of the derivative 8 (white powder, 30% yield) are obtained.

Analysis: $C_{10}H_9NO_3$; Calculated: C 62.82; H 4.74; N 7.33; Found: C 62.84; H 4.75; N 7.29.

Example 5

Preparation of the compound No. 12 of Table I
[5,6-Bis(trimethylsilyloxy)indole]

0.3 g (0.002 mole) of 5,6-dihydroxyindole is added to 0.81 g (0.004 mole) of N,O-bis(trimethylsilyl)-acetamide while stirring at room temperature. When the dissolution is complete, 2 ml of dichloromethane are added and this solution is passed through a column of silica 60, eluting with dichloromethane. The first fraction obtained is concentrated in a rotary evaporator and then dried under vacuum. 0.42 g (yield: 71%) of white crystals of the derivative 12 is thereby obtained.

Analysis: $C_{14}H_{23}NO_2Si_2$; Calculated: C 57.29; H 7.90; N 4.77; Found: C 57.39; H 7.96; N 4.72.

Example 6

Preparation of the compound No. 13 of Table I 5,6-[(1-Ethoxyethylidene)dioxy]indole In a round-bottomed flask equipped with a distillation system, 14.6 ml (0.08 mole of triethyl orthoacetate and 3 g (0.02 mole) of 5,6-dihydroxyindole are heated on an oil bath brought to 120° C., in such a way that the ethanol formed distils continuously (reaction time: 4 hours). The excess triethyl orthoacetate is distilled off and the fraction of boiling point 160° C. at $1.06 \times 10^2$ Pa isolated. The colourless oil obtained crystallizes to give the compound 13 (2.71 g; yield: 62%).

Analysis: $C_{12}H_{13}NO_3$; Calculated: C 65.74; H 5.98; N 6.39; Found: C 65.34; H 6.01; N 6.29.

Example 7

Preparation of the compound No. 11 of Table I
5-Hydroxy-6-(trimethylsilyloxy)indole and 6-hydroxy-5-(trimethylsilyloxy)indole A solution of 200 ml of dry tetrahydrofuran containing 3 g (0.02 mole) of 5,6-dihydroxyindole and 8.2 g (0.04 mole) of bis(trimethylsilyl)urea is stirred for 2 and a half hours. After the addition of 100 ml of toluene, the organic phase is washed with water, and it is concentrated under vacuum after being dried over sodium sulphate. The 5 g of residue are passed rapidly through a silica column (eluent: $CH_2Cl_2$). As well as the disilyl derivative 12, 0.5 g of the derivative 11 (yield: 11%), a 30:70 mixture of the two monosilyl derivatives as shown by the proton NMR spectrum, is recovered.

Analysis: $C_{11}H_{15}NO_2Si$; Calculated: C 59.69; H 6.83; N 6.33; Found: C 59.27; H 6.89; N 6.33.

Example 8

Preparation of the compound No. 14 of Table I
(5,6-dihydroxyindole cyclic phosphodiester)

6.06 g (0.06 mole) of triethylamine are added in the course of 15 minutes at room temperature, under nitrogen and in the absence of moisture, to a solution of 4.14 g (0.06 mole) of 1,2,4-triazole and 1.84 ml (0.02 mole) of phosphorus oxychloride in 150 ml of dry dioxane. The mixture is left with stirring for 40 minutes at 20° C. The triethylamine hydrochloride formed is filtered off, avoiding contact between the filtrate and the air. The solution of phosphoryltris(1,2,4-triazole) obtained is added in the course of 2 hours at 20° C. under nitrogen to a solution of 2.68 g (0.018 mole) of 5,6-dihydroxyindole. The mixture is then stirred for 3 and a half hours and left standing overnight, and the precipitates obtained (2.9 g dry) is filtered off. This precipitate is stirred for 1 hour at room temperature in 100 ml of water, filtered off again and dried. The derivative 14 is recovered (1 g; yield: 26%). The NMR spectrum is in agreement with the expected structure.

Example 9

Preparation of the compound No. 15 of Table I
5,6-Thiocarbonyldioxyindole

A solution of 2.82 g (0.0158 mole) of thiocarbonyldiimidazole in 400 ml of toluene is added dropwise at 60° C. and under nitrogen to a solution of 1.49 g (0.01 mole) of 5,6-dihydroxyindole in 100 ml of isopropyl ether and 50 ml of toluene. The mixture is left with stirring for 2 hours at 60° C. The reaction mixture is concentrated under vacuum. 200 ml of water are added to the residue obtained. The pale yellow precipitate is filtered off and washed copiously with water. It is redissolved in 50 ml of acetone and reprecipitated with 300 ml of water. After drying under a vacuum of 13.3 Pa, 1.2 g (yield: 63%) of the derivative 15 (yellowed-tinged powder) is obtained.

Analysis: $C_9H_5NO_2S$; Calculated: C 56.56; H 2.64; N 7.33; S 16.77; Found: C 56.57; H 2.58; N 7.19; S 16.64.

Example 10

Preparation of the compound No. 9 of Table I
(5-Butoxy-6-hydroxyindole)

1st stage

Preparation of 6-benzyloxy-5-butoxyindole

A mixture of 5-butoxy-4-hydroxy-2-nitrobenzaldehyde (31 g; 0.13 mole), benzyl chloride (20.2 g; 0.16 mole) and potassium carbonate (22.11 g; 0.16 mole) in 80 ml of dimethylformamide is heated for 2 hours under reflux with stirring. The reaction mixture is poured into 200 ml of ice-cold water and the precipitate filtered off. After recrystallization in a hexane/toluene mixture, 4-benzyloxy-5-butoxy-2-nitrobenzaldehyde (30.2 g; yield: 71%; yellow powder) is obtained; melting point 94° C.

Nitromethane (10.1 ml; 0.185 mole) is added to a mixture of the above derivative (26.3 g; 0.08 mole) in 90 ml of glacial acetic acid and dry ammonium acetate (8.85 g; 0.115 mole). After 5 hours' refluxing, the reaction mixture is poured into 200 ml of ice-cold water. The brown precipitate is filtered off and recrystallized in ethanol. 4-Benzyloxy-5-butoxy-2,β-dinitrostyrene (18.4 g; yield 62%; yellow powder) is obtained; melting point 152° C.

A solution of 160 ml of absolute ethanol and 80 ml of acetic acid is brought to 60° C. To this solution, activated iron (48 g) is added; the mixture is brought to 80°-85° C. with thorough stirring and the derivative obtained above (8.9 g; 0.024 mole) is added in the course of 15 minutes. After 30 minutes' stirring at 85° C., the ferric sludge is filtered off and rinsed with 300 ml of acetic acid followed by 300 ml of ethanol. The filtrate is diluted with ice. The precipitate formed is filtered off, washed with water and dried. After passage through a column of silica 60 (eluent: $CH_2Cl_2$), the expected product is recovered (5 g; 70% yield).

Analysis: $C_{19}H_{21}NO_2$; Calculated: C 77.26; H 7.16; N 4.74; Found: C 77.36; H 7.17; N 4.72.

2nd stage

Preparation of 5-butoxy-6-hydroxyindole

The above derivative (4 g; 0.0135 mole) was hydrogenated under 50 atmospheres of hydrogen in a bomb with 40 ml of ethanol and 0.06 g of palladinized charcoal (10% palladium) for 3 hours. After filtration and evaporation of the solvent, the residue was recrystallized in a benzene/hexane mixture to give the derivative 9 (2.5 g; 90% yield).

Analysis: $C_{12}H_{15}NO_2$; Calculated: C 70.22; H 7.37; N 6.82; Found: C 70.31; H 7.28; N 6.77.

Example 11

Preparation of the compound No. 10 of Table I
(6-Butoxy-5-hydroxyindole)

1st stage

5-Benzyloxy-6-butoxyindole 8.6 g of activated iron are added at 60° C. to a solution of 28 ml of absolute ethanol and 14 ml of acetic acid. The mixture is kept for 15 minutes at 80° C. and 5-benzyloxy-4-butoxy-2,β-dinitrostyrene (1.6 g; 0.0043 mole) is added. The mixture is left at 80° C. for 1 hour, and the ferric sludge is filtered off and rinsed with 40 ml of ethanol and 40 ml of acetic acid. The filtrate is diluted with 100 ml of ice-cold water. After extraction of the solution with methylene chloride and drying of the organic phase over sodium sulphate, the organic phase is concentrated and chromatographed on silica 60 (eluent: toluene/$CH_2Cl_2$, 50:50). 0.5 g (40% yield) of the expected derivative is obtained.

Analysis: $C_{19}H_{21}NO_2$; Calculated: C 77.26; H 7.16; N 4.74; Found: C 77.06; H 7.14; N 4.82.

2nd stage

Preparation of 6-butoxy-5-hydroxyindole

The above derivative (0.5 g; 0.0017 mole) was hydrogenated under 50 atmospheres of hydrogen in a bomb with 5 ml of absolute ethanol and 70 mg of palladinized charcoal coal (10% palladium) for 2 hours. After filtration and evaporation of the solvent, the residue was purified by chromatography on silica 60 (eluent: $CH_2Cl_2$) to give the derivative 10 (0.19 g, beige powder; 55% yield).

Analysis: $C_{12}H_{15}NO_2$; Calculated: C 70.22; H 7.37; N 6.82; Found: C 70.11; H 7.37; N 6.75.

Example 12

Preparation of the compound No. 16 of Table I
(5-Methoxy-6-trimethylsilyloxyindole)

6-Hydroxy-5-methoxyindole 1 (2.04 g; 0.0125 mole) and N,O-bis(trimethylsilyl)acetamide (5.08 g; 0.025 mole) are mixed at room temperature until solubilization is complete. After chromatography on a column of silica 60 (eluent: $CH_2Cl_2$), the derivative 16 is obtained (2.54 g; 86% yield).

Analysis: $C_{12}H_{17}NO_2Si$; Calculated: C 61.24; H 7.28; N 5.95; Found: C 61.30; H 7.32; N 6.01.

Example 13

Preparation of the compound No. 17 of Table I
5,6-Bis(trimethylsilyloxy)-2-methylindole 5,6-Dihydroxy-2-methylindole (90 mg; $5.5 \times 10^{-4}$ mole) and N,O-bis(trimethylsilyl)acetamide (220 mg; $1.1 \times 10^{-3}$ mole) are stirred at room temperature until solubilization is complete. The product obtained is purified on a column of silica 60 (eluent: toluene/$CH_2Cl_2$, 50:50). The derivative 17 is obtained (0.14 g; 83% yield).

Analysis: $C_{15}H_{25}NO_2Si_2$; Calculated: C 58.58; H 8.19; N 4.55; Found: C 58.54; H 8.16; N 4.60.

Example 14

Preparation of the compound No. 18 of Table I
(5,6-Carbonyldioxy-2-methylindole)

Carbonyldiimidazole (1.67 g; 0.0103 mole) dissolved in 300 ml of toluene is added under reflux to the 5,6-dihydroxy-2-methylindole derivative (0.51 g; 0.0031 mole) dissolved in 50 ml of isopropyl ether. After two hous under reflux, 200 ml of water are added and the toluene phase is separted and then dried over sodium sulphate. The solvent is evaporated off and the product recrystallized in a 50:50 mixture of water and ethanol. The derivative 18 is obtained (0.45 g; 76% yield).

Analysis: $C_{10}H_7NO_3$; Calculated: C 63.49; H 3.73; N 7.40; Found C 63.44; H 3.75; N 7.06.

Examples 15 and 16

Preparation of the compounds Nos. 19 and 20 of Table I

[(5 or 6)-Hydroxy-(6 or 5)-myristoyloxyindole and 5,6-dimyristoyloxyindole]

A solution of 5,6-dihydroxyindole (2.98 g; 0.02 mole) in 300 ml of THF and M-myristoylimidazole (5.57 g; 0.02 mole) is brought to reflux for 4 hours. After concentration under vacuum, the residue is chromatographed on a column of silica 60 (eluent: $CH_2Cl_2$) to give the compound 20 (2.6 g; 23% yield);

Analysis: $C_{36}H_{59}NO_4$; Calculated: C 75.88; H 10.44; N 2.46; Found: C 75.60; H 10.40; N 2.71. and the compound 19 (2.7 g; 38% yield), which is a 70:30 mixture of the two monoesters, as shown by the proton NMR spectrum.

Analysis: $C_{22}H_{33}NO_3$; Calculated: C 73.50; H 9.25; N 3.90; Found: C 73.59; W 9.25; N 3.87.

Examples 17 and 18

Preparation of the compounds Nos. 21 and 22 of Table I

[(5 or 6)-Hydroxy-(6 or 5)-oleoyloxyindole and 5,6-dioleoyloxyindole]

N-Oleoylimidazole dissolved in 100 ml of tetrahydrofuran is added dropwise at 20° C. under nitrogen to a solution of 5,6-dihydroxyindole (2.98 g; 0.02 mole) in 50 ml of tetrahydrofuran. The mixture is brought to reflux for 4 hours. The solvent is removed under vacuum and the residue chromatographed on silica 60 (eluent: toluene/$CH_2Cl_2$, 50:50) to give the compound 22 (1.9 g; 14% yield);

Analysis: $C_{44}H_{71}NO_4$; Calculated: C 77.94; H 10.55; N 2.06; Found: C 77.84; H 10.34; N 2.11. and the compound 21 (eluent: $CH_2Cl_2$) (5 g; 60% yield), which is a 70:30 mixture of the two monoesters, as shown by the proton NMR spectrum.

Analysis: $C_{26}H_{39}NO_3$; Calculated: C 75.50; H 9.50; N 3.39; Found: C 75.62; H 9.54; N 3.41.

Example 19

Preparation of the compound No. 23 of Table I

[5,6-Bis(trimethylsilyloxy)-2-carbethoxyindole]

5,6-Dihydroxy-2-carbethoxyindole (442 mg; 0.002 mole) and N,O-bis(trimethylsilyl)acetamide (814 mg; 0.004 mole) are stirred at 40° C. for 30 minutes. The solution obtained is chromatographed on silica 60 (eluent: toluene/$CH_2Cl_2$, 50:50). After concentration under vacuum, the derivative 23 is obtained (0.59 g; 73% yield).

Analysis: $C_{17}H_{27}NO_4Si_2$; Calculated: C 55.85; H 7.44; N 3.83; Found: C 55.90; H 7.55; N 3.77.

Example 20

Preparation of the compound No. 24 of Table I

[5,6-Bis(trimethylsilyloxy)-2-(trimethylsilyloxycarbonyl)indole]

5,6-Dihydroxy-2-carboxyindole (0.2 g; 0.00103 mole) and N,O-bis(trimethylsilyl)acetamide (2.5 g; 0.0124 mole) are brought to 60° C. for 1 hour with stirring. The solution is poured into 50 g of ice and the precipitate filtered off and washed with water. It is taken up in dichloromethane and dried over sodium sulphate. After evaporation under vacuum, the derivative 24 is obtained (0.35 g; 83% yield). MS (70 eV) for $C_{18}H_{31}NO_4Si_3$: 409 ($M^+$, 12.5), 337(41), 319(14), 232(30), 75(75) and 73(100).

Example 21

Preparation of the compound No. 25 of Table I 5,6-Bis(trimethylsilyloxy)-3-methylindole 5,6-Dihydroxy-3-methylindole (0.3 g; 0.0018 mole) and N,O-bis(trimethylsilyl)acetamide (0.61 g; 0.0036 mole) are stirred for 30 minutes at room temperature. The solution obtained is chromatographed on silica 60 (eluent: $CH_2Cl_2$) to give the derivative 25 (0.43 g; 78% yield).

Analysis: $C_{15}H_{25}NO_2Si_2$; Calculated: C 58.57; H 8.19; N 4.55; Found: C 58.55; H 8.18; N 4.53.

Example 22

Preparation of the compound No. 26 of Table I (6-Hexadecyloxy-5-methoxyindole)

6-Hydroxy-5-methoxyindole (2 g; 0.0123 mole) dissolved in 10 ml of dimethylformamide (DMF) is introduced dropwise in the course of 20 minutes into a mixture of 1-bromohexadecane (4.5 g; 0.0148 mole) and potassium carbonate (1.87 g; 0.0135 mole) in 45 ml of DMF at 70° C. and under nitrogen. The reaction mixture is stirred under nitrogen at 80° C. for 3 and a half hours. The blackish mixture is poured into ice-cold water with stirring and the brownish solid formed is immediately filtered off and washed with water. It is taken up in dichloromethane and dried over sodium sulphate. After chromatography on silica 60 (eluent: toluene/$CH_2Cl_2$, 50:50), and recrystallization in hexane, the derivative 26 is obtained (1.66 g; 35% yield).

Analysis: $C_{25}H_{41}NO_2$; Calculated: C 77.47; H 10.66; N 3.61; Found: C 77.35; H 10.62; N 3.71.

Examples 23 and 24

Preparation of the compounds Nos. 27 and 28 of Table I (6-Hexadecyloxy-5-hydroxyindole and 5-hexadecyloxy-6-hydroxyindole)

Potassium carbonate (2.76 g; 0.02 mole), 5,6-dihydroxyindole (3 g; 0.02 mole) and 1-bromohexadecane (6.14 g; 0.02 mole) are introduced successively at 50° C. under nitrogen and with stirring into 30 ml of dry DMF. The mixture is heated to 60°-70° C. for 2 and a half hours. The blackish mixture is poured into ice-cold water with brisk stirring and the dark brown precipitate is immediately filtered off, washed with water, taken up with dichloromethane and dried for 5 minutes over sodium sulphate. The solution is concentrated and chromatographed on silica 60 (eluent: toluene/$CH_2Cl_2$, 50:50) to give, in fractions 14 to 18, the compound 27 (1.8 g; 24% yield);

Analysis: $C_{24}H_{39}NO_2$; Calculated: C 77.16; H 10.52; N 3.75; Found: C 77.44; H 10.54; N 3.85. and, in fractions 23 to 33, the compound 28 (0.8 g, 11% yield).

Analysis: $C_{24}H_{39}NO_2$; Calculated: C 77.16; H 10.52; N 3.75; Found: C 77.07; H 10.59; N 3.91.

Examples 25 and 26

Preparation of the compounds Nos. 29 and 30 of Table I

[5,6-Dipivaloyloxyindole and (5 or 6)-hydroxy-(6 or 5)-pivaloyloxyindole]

N,N'-Carbonyldiimidazole (1.78 g; 0.011 mole) is added to a solution of pivalic acid (1.122 g; 0.011 mole) in 25 ml of methylene chloride. The mixture is left with stirring a room temperature until the evolution of $CO_2$ gas ceases (1 hour). 5,6-Dihydroxyindole (1.64 g; 0.011 mole) is added under nitrogen and at room temperature, and the mixture is left with stirring for 4 hours. The organic phase is washed with water and dried over sodium sulphate. After separation on a chromatographic column of silica 60, there are obtained the derivative 29 (eluent: toluene/$CH_2Cl_2$ 50:50) (0.59 g; 17% yield);

Analysis: Chd $18H_{23}NO_4$; Calculated: C 68.12; H 7.30; N 4.41; Found: C 68.02; H 7.27; N 4.49. and the derivative 30 (eluent: $CH_2Cl_2$) (1.74 g; 68% yield).

Analysis: $C_{13}H_{15}NO_3$; Calculated: C 66.94; H 6.48; N 6.00; Found: C 66.77; H 6.49; N 5.90.

Examples 27 and 28

Preparation of the compounds Nos. 31 and 32 of Table I 5,6-Dihexanoyloxyindole and (5 or 6)-hexanoyloxy(6 or 5)-hydroxyindole In an identical manner to the previous examples, hexanoic acid (2.65 g; 0.022 mole) was treated in methylene chloride (50 ml) with N,N'-carbonyldiimidazole (3.75 g; 0.022 mole) and 5,6-dihydroxyindole (3.28 g; 0.022 mole). The derivative 31 was obtained (1.90 g; 25% yield);

Analysis: $C_{20}H_{27}NO_4$; Calculated: C 69.54; H 7.89; N 4.05; Found: C 69.26; H, 7.93; N 3.96. and the derivative 32 (3.21 g; 59% yield).

Analysis: $C_{14}H_{17}NO_3$; Calculated: C 68.00; H 6.93; N 5.66; Found: C 67.65; H 6.98; N 5.64.

Examples 29 and 30

Preparation of the compounds Nos. 33 and 34 of Table I 5,6-Dibutanoyloxyindole and (5 or 6)-butanoyloxy(6 or 5)-hydroxyindole In an identical manner to the previous examples, butanoic acid (2.9 g; 0.033 mole) was treated in methylene chloride (75 ml) with N,N'-carbonyldiimidazole (5.35 g; 0.033 mole) and 5,6-dihydroxyindole (4.92 g; 0.033 mole). The derivative 33 was obtained (2.77 g; 29% yield);

Analysis: $C_{16}H_{19}NO_4$; Calculated: C 66.42; H 6.62; N 4.84; Found: C 66.65; H 6.64; N 4.76. and the derivative 34 (2.64 g; 36.5% yield).

Analysis: $C_{12}H_{13}NO_3$; Calculated: C 65.74; H 5.98; N 6.39; Found: C 65.46; H 5,94; N 6.14.

EXAMPLES OF APPLICATION OF THE COMPOSITIONS

The following compositions are prepared:

| SOLUTION A | | |
|---|---|---|
| Copper sulphate pentahydrate | | 1.0 g |
| Monoethanolamine | qs pH | 9.5 |
| Demineralized water | qs | 100.0 g |
| SOLUTION B1 | | |
| 6-Hydroxy-5-methoxyindole | | 1.0 g |
| Ethyl alcohol | | 20.0 g |
| Sodium hydroxide | qs pH | 8.5 |
| Demineralized water | qs | 100.0 g |
| SOLUTION B2 | | |
| 5,6-Bis(trimethylsilyloxy)indole | | 1.0 g |
| Ethyl alcohol | | 50.0 g |
| Sodium hydroxide | qs pH | 10.5 |
| Demineralized water | qs | 100.0 g |
| SOLUTION B3 | | |
| 5-Hydroxy-6-methoxyindole | | 1.3 g |
| Ethyl alcohol | | 20.0 g |
| Sodium hydroxide | qs pH | 8.5 |
| Demineralized water | qs | 100.0 g |
| SOLUTION B4 | | |
| Mixture of compounds (5 or 6)-acetoxy-(6 or 5)-hydroxyindole | | 1.0 g |
| Ethyl alcohol | | 20.0 g |
| Spontaneous pH | | 5.4 |
| Demineralized water | qs | 100.0 g |
| SOLUTION B5 | | |
| 5,6-Carbonyldioxyindole | | 1.25 g |
| 20% strength sodium hydroxide | | 0.05 g |
| Ethanol | qs | 100.0 g |

Example 1

The solution A is applied on locks of grey hair which is 90% white.

After 5 minutes' exposure, the hair is rinsed.

The solution B1 is then applied for 5 minutes.

After rinsing and drying, a golden pearly dark blend colouration is obtained on these locks.

Example 2

On the same type of hair as for Example 1, the solution A is first applied for 5 minutes.

After rinsing, the solution B2 is applied for 5 minutes and rinsed.

The hair is dried.

The colouration obtained is a matt dark blond. If the hair is permanent-waved, the shade obtained is then chestnut-brown.

Example 3

On permanent-waved grey hair which is 90% white, impregnated for 5 minutes with the solution A and rinsed, the solution B3 is applied for 5 minutes.

After rinsing and drying, a matt blond colouration is obtained.

Example 4

By replacing the solution B3 in Example 3 by the solution B4, a virtually black final shade is obtained.

If the pH of the solution B4 is adjusted to pH 8.5 with sodium hydroxide, the final shade is a deep black.

Example 5

A lock of sensitized hair is immersed in the solution B5 for 5 minutes.

The hair is rinsed and dried and a pale ash-blond colour is obtained.

Example 6

If the solution B1 is applied on grey hair which is 90% white and which has not been pretreated with the solution A, a pearly blond colouration is obtained after 5 minutes' exposure followed by rinsing and drying.

Example 7

A permanent-waved lock of grey hair which is 90% white is immersed in the solution B2.

The hair is rinsed after 5 minutes' exposure and dried. A natural dark blond shade is obtained.

We claim:

1. A dye composition for keratinous fibers comprises, in a cosmetically acceptable medium and in an amount ranging from 0.01 to 5 percent by weight based on the total weight of said composition, at least one dye having the formula

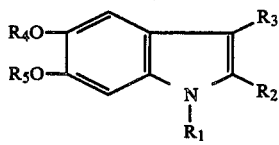

(I)

wherein $R_1$ represents hydrogen, lower alkyl or $-SiR_9R_{10}R_{11}$, $R_2$ and $R_3$, each independently, represent hydrogen, lower alkyl, lower alkoxy carbonyl or $-COOSiR_9R_{10}R_{11}$, $R_4$ and $R_5$, each independently, represent a member selected from the group consisting of linear or branched $C_1-C_{20}$ alkyl, formyl, linear or branched $C_2-C_{20}$ acyl, linear or branched $C_3-C_{20}$ alkenoyl, $-SiR_9R_{10}R_{11}$, $-P(O)(OR_6)_2$ and $R_6OSO_2-$, or one of $R_4$ and $R_5$ is hydrogen and the other has the meaning given above, with the proviso that $R_4$ and $R_5$ are not simultaneously acetyl, or $R_4$ and $R_5$ together with the oxygen atoms to which they are attached form a ring containing a carbonyl group, a thiocarbonyl group, a $>P(O)OR_6$ group or a $>CR_7R_8$ group, $R_6$ represents hydrogen or lower akyl, $R_7$ represents hydrogen or lower alkyl, $R_8$ represents lower alkoxy, monoalkylamino or dialkylamino, $R_9$, $R_{10}$ and $R_{11}$, each independently, represent linear or branched lower alkyl, and the cosmetically acceptable alkali metal, alkaline earth metal, ammonia or amine salts of the dye of formula I, said dye composition also including an effective amount of at least one of a surfactant, an anionic polymer, a nonionic polymer a cationic polymer, an amphoteric polymer, a thickening agent, a penetrating agent, a swelling agent, a sequestering agent, an antioxidant, a buffer, an electrolyte and a perfume.

2. The dye composition of claim 1 wherein said lower alkyl contains 1-6 carbon atoms and said lower alkoxy contains 1-6 carbon atoms.

3. The dye composition of claim 1 wherein said dye of formula I is selected from the group consisting of 6-hydroxy-5-methoxyindole,
5-hydroxy-6-methoxyindole,
6-acetoxy-5-methoxyindole,
(5 or 6)-acetoxy-(6 or 5)-hydroxyindole,
5,6-carbonyldioxyindole,
(5 or 6)-formyloxy-(6 or 5)-hydroxyindole,
(5 or 6)-acetoxy-(6 or 5)-formyloxyindole,
6-formyloxy-5-methoxyindole,
5-butoxy-6-hydroxyindole,
6-butoxy-5-hydroxyindole,
(5 or 6)-hydroxy-(6 or 5)-trimethylsilyloxyindole,
5,6-bis(trimethylsilyloxy)indole,
5,6-[(1-ethoxyethylidene)dioxy]indole,
5,6-dihydroxyindolecyclic phosphodiester,
5,6-thiocarbonyldioxyindole,
5-methoxy-6-trimethylsilyloxyindole,
5,6-bis-(trimethylsilyloxy)-2-methylindole,
5,6-carbonyldioxy-2-methylindole,
(5 or 6)-hydroxy-(6 or 5)-myristoyloxyindole,
5,6-dimyristoyloxyindole,
(5 or 6)-hydroxy-(6 or 5)-oleoyloxyindole,
5,6-dioleoyloxyindole,
5,6-bis(trimethylsilyloxy)-2-carbethoxyindole,
5,6-bis(trimethylsilyloxy)-2-(trimethylsilyloxy carbonyl)indole,
5,6-bis(trimethylsilyloxy)-3-methylindole,
6-hexadecyloxy-5-methoxyindole,
6-hexadecyloxy-5-hydroxyindole,
5-hexadecyloxy-6-hydroxyindole,
5,6-dipivaloyloxyindole,
(5 or 6)-hydroxy-(6 or 5)-pivaloyloxyindole,
5,6-dihexanoyloxyindole,
(5 or 6)-hexanoyloxy-(6 or 5)-hydroxyindole,
5,6-dibutanoyloxyindole and
(5 or 6)-butanoyloxy-(6 or 5)-hydroxyindole.

4. The dye composition of claim 1 where in the dye of formula I $R_1$ represents hydrogen, $R_2$ and $R_3$, each independently, represent hydrogen or lower alkyl, one of $R_4$ and $R_5$ represents linear or branched $C_1-C_{20}$ alkyl, linear or branched $C_2-C_{20}$ acyl or linear or branched $C_3-C_{20}$ alkenoyl and the other represents hydrogen, or $R_4$ and $R_5$ simultaneously represent $SiR_9R_{10}R_{11}$ wherein $R_9$, $R_{10}$ and $R_{11}$ have the meanings given in claim 1.

5. The dye composition of claim 1 wherein said dye of formula I is present in an amount ranging from 0.03 to 2.5 percent by weight based on the total weight of said composition.

6. The dye composition of claim 1 in the form of a liquid, a thickened liquid, a cream, a gel, an oil or a powder.

7. The dye composition of claim 1 wherein said cosmetically acceptable medium is an aqueous medium having a pH ranging from 3.5 to 11.

8. The dye composition of claim 7 wherein said aqueous medium also contains a surfactant present in an amount ranging from 0.1 to 55 percent by weight and an organic solvent present in an amount ranging from 1 to 60 percent by weight, based on the total weight of said composition.

9. The dye composition of claim 8 wherein said organic solvent is a lower alcohol, ethyleneglycol monomethyl ether, ethyleneglycol monoethyl ether, ethyleneglycol monobutyl ether or ethyleneglycol monoethyl ether acetate.

10. The dye composition of claim 1 which contains an anionic, nonionic, cationic or amphoteric polymer or a mixture thereof, in an amount ranging from 0.1 to 5 percent by weight based on the total weight of said composition.

11. The dye composition of claim 1 wherein said cosmetically acceptable medium is an anhydrous medium.

12. The dye composition of claim 11 wherein said anhydrous medium is selected from the group consisting of a saturated monohydric alcohol, ethyleneglycol monomethyl ether, ethyleneglycol monoethyl ether, ethyleneglycol monobutyl ether and ethyleneglycol monoethyl ether acetate.

13. A process for dyeing keratinous fibers comprising applying to said fibers in an amount effective to dye said fibers a dye composition comprising, in a cosmetically acceptable medium, at least one dye having the formula

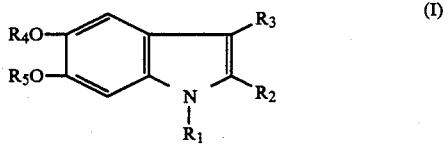

wherein
R$_1$ represents hydrogen, lower alkyl or —SiR$_9$R$_{10}$R$_{11}$,
R$_2$ and R$_3$, each independently, represent hydrogen, lower alkyl, carbonyl, lower alkoxy carbonyl or —COOSiR$_9$R$_{10}$R$_{11}$,
R$_4$ and R$_5$, each independently, represent a member selected from the group consisting of linear or branched C$_1$–C$_{20}$ alkyl, formyl, linear or branched C$_2$–C$_{20}$ acyl, linear or branched C$_3$–C$_{20}$ alkenoyl, —SiR$_9$R$_{10}$R$_{11}$, —P(O)(OR$_6$)$_2$, or one of R$_4$ and R$_5$ is hydrogen and the other has the meaning given above, with the proviso that R$_4$ and R$_5$ are not simultaneously acetyl,
or R$_4$ and R$_5$ together with the oxygen atoms to which they are attached form a ring containing a carbonyl group, a thiocarbonyl group, a >P(O)OR$_6$ group or a >CR$_7$R$_8$ group,
R$_6$ represents hydrogen or lower alkyl,
R$_7$ represents hydrogen or lower alkyl,
R$_8$ represents lower alkoxy, monoalkylamino or dialkylamino,
R$_9$, R$_{10}$ and R$_{11}$, each independently, represent linear or branched lower alkyl,
and the cosmetically acceptable alkali metal, alkaline earth metal, ammonia or amine salts of the dye of formula I,
said dye of formula I being present in said composition in an amount ranging from 0.01 to 5 percent by weight based on the total weight of said composition.

14. The process of claim 13 comprising initially applying to said keratinous fibers said dye of formula I in an acidic or neutral medium, permitting said dye containing acidic or neutral medium to remain in contact with said fibers for a period of time ranging from 5 to 60 minutes, wringing said fibers dry and contacting said fibers with an oxidizing agent.

15. The process of claim 14 wherein said oxidizing agent contains an oxidation catalyst selected from the group consisting of a cobalt salt, an iron salt, a manganese salt, a copper salt and an aluminum salt.

16. The process of claim 18 comprising applying to said keratinous fibers said dye of formula I in an alkaline medium containing, as an alkalinizing agent, ammonia or an amine.

17. The process of claim 16 which comprises repeating the application to said keratinous fibers of said dye of formula I in said alkaline medium for a number of times sufficient to impart a desired shade to said keratinous fibers.

18. The process of claim 16 which includes contacting said fibers with an oxidizing agent.

19. The process of claim 16 which includes adding an oxidizing agent to said alkaline medium containing said dye of formula I, just prior to the application of said medium to said fibers.

20. The process of claim 13 which comprises, in one stage, contacting said fibers with a metal salt before or after applying in another stage said dye composition to said fibers and rinsing said fibers between said stages.

21. The process of claim 13 which includes, subsequent to applying said dye composition to said fibers, rinsing said fibers and contacting the rinsed fibers with a hydrogen peroxide solution so as to lighten the tint resulting from the application of said dye composition to said fibers.

22. The process of claim 13 wherein said dye composition also contains an anionic, nonionic, cationic or amphoteric polymer, or a mixture thereof, and said dye composition is mixed, just prior to application to said fibers, with an aqueous cosmetic vehicle containing cosmetically acceptable additives.

23. A hair dyeing kit comprising a plurality of compartments, one of said compartments containing the dye composition of claim 1 and another of said compartments containing a metal salt.

24. The hair dye kit of claim 23 which also contains yet another compartment containing an oxidizing agent.

25. A compound having the formula

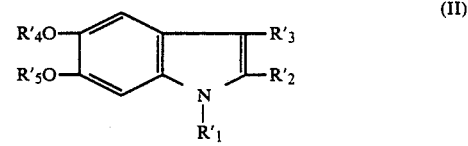

wherein
R′$_1$ represents hydrogen or lower alkyl,
R′$_2$ and R′$_3$, each independently, represent hydrogen, lower alkyl, carboxyl, lower alkoxy carbonyl or —COOSi(CH$_3$)$_3$,
one of R′$_4$ and R′$_5$ is selected from the group consisting of linear or branched C$_{10}$–C$_{20}$ acyl, and —P(O)(OR$_6$)$_2$ and the other is selected from the group consisting of hydrogen, C$_1$–C$_8$ alkyl, formyl, C$_2$–C$_9$ acyl or aralkyl,
or one or both of R′$_4$ and R′$_5$ represent —Si(CH$_3$)$_3$ when R′$_1$ is other than methyl,
or R′$_4$ and R′$_5$ together with the oxygen atoms to which they are attached form a ring containing a carbonyl group when one of R′$_1$, R′$_2$ and R′$_3$ is other than hydrogen, a thiocarbonyl group, a >P(O)OR$_6$ group or a >CR$_7$R$_8$ group,
R$_6$ represents hydrogen or lower alkyl,
R$_7$ represents hydrogen or lower alkyl and
R$_8$ represents lower alkoxy, monoalkylamino or dialkylamino,
and the alkali metal, alkaline earth metal, ammonia or amine salts of the compound of formula II.

* * * * *